(12) United States Patent
Seneca et al.

(10) Patent No.: US 11,980,682 B2
(45) Date of Patent: May 14, 2024

(54) COMPOSITION FOR DYEING KERATIN FIBRES, COMPRISING AT LEAST ONE COPOLYMER DERIVED FROM THE POLYMERIZATION OF AT LEAST ONE CROTONIC ACID MONOMER AND OF AT LEAST ONE VINYL ESTER MONOMER AND A FATTY AMINE

(71) Applicant: L'OREAL, Paris (FR)

(72) Inventors: David Seneca, Saint-Ouen (FR); Lindsay Menzer, Saint-Ouen (FR); Malayphone Sananikone, Saint-Ouen (FR); Delphine Charrier, Saint-Ouen (FR)

(73) Assignee: L'OREAL, Paris (FR)

( * ) Notice: Subject to any disclaimer, the term of this patent is extended or adjusted under 35 U.S.C. 154(b) by 781 days.

(21) Appl. No.: 16/975,871

(22) PCT Filed: Jun. 18, 2019

(86) PCT No.: PCT/EP2019/066047
§ 371 (c)(1),
(2) Date: Aug. 26, 2020

(87) PCT Pub. No.: WO2020/002051
PCT Pub. Date: Jan. 20, 2020

(65) Prior Publication Data
US 2020/0405616 A1  Dec. 31, 2020

(30) Foreign Application Priority Data

Jun. 28, 2018 (FR) ..................... 1855867

(51) Int. Cl.
| | |
|---|---|
| *A61Q 5/10* | (2006.01) |
| *A61K 8/44* | (2006.01) |
| *A61K 8/81* | (2006.01) |
| *A61K 8/892* | (2006.01) |
| *A61K 8/898* | (2006.01) |
| *A61Q 5/06* | (2006.01) |

(52) U.S. Cl.
CPC ............ *A61K 8/8147* (2013.01); *A61K 8/442* (2013.01); *A61K 8/892* (2013.01); *A61K 8/898* (2013.01); *A61Q 5/065* (2013.01); *A61K 2800/43* (2013.01); *A61K 2800/48* (2013.01)

(58) Field of Classification Search
CPC ...... A61K 8/8147; A61K 8/442; A61K 8/892; A61K 8/898; A61K 2800/43; A61K 2800/48; A61K 2800/432; A61K 8/19; A61K 8/42; A61Q 5/065
USPC .......................................................... 8/405
See application file for complete search history.

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 3,716,633 A | 2/1973 | Viout et al. |
| 3,810,977 A | 5/1974 | Levine et al. |
| 3,966,403 A | 6/1976 | Papantoniou et al. |
| 3,966,404 A | 6/1976 | Papantoniou et al. |
| 4,185,087 A | 1/1980 | Morlino |
| 4,237,243 A | 12/1980 | Quack et al. |
| 4,578,266 A | 3/1986 | Tietjen et al. |
| 4,957,732 A | 9/1990 | Grollier et al. |
| 5,645,609 A | 7/1997 | Andrean et al. |
| 5,990,479 A | 11/1999 | Weiss et al. |
| 6,106,577 A | 8/2000 | Audousset et al. |
| 6,225,198 B1 | 5/2001 | Alivisatos et al. |
| 2007/0237736 A1 | 10/2007 | Burgo et al. |
| 2017/0202763 A1* | 7/2017 | Manneck ................. A61K 8/41 |

FOREIGN PATENT DOCUMENTS

| | | |
|---|---|---|
| EP | 0186507 A2 | 7/1986 |
| EP | 0342834 A2 | 11/1989 |
| EP | 0530974 A1 | 3/1993 |
| EP | 1184426 A2 | 3/2002 |
| EP | 1714677 A1 | 10/2006 |
| FR | 1222944 A | 6/1960 |
| FR | 1564110 A | 4/1969 |
| FR | 1580545 A | 9/1969 |
| FR | 2265781 A1 | 10/1975 |
| FR | 2265782 A1 | 10/1975 |
| FR | 2416723 A1 | 9/1979 |
| FR | 2439798 A1 | 5/1980 |
| FR | 2679771 A1 | 2/1993 |
| FR | 2741530 A1 | 5/1997 |
| GB | 922457 A | 4/1963 |
| JP | 05-017710 A | 1/1993 |
| JP | 07-258460 A | 10/1995 |
| JP | 09-188830 A | 7/1997 |
| JP | 10-158450 A | 6/1998 |

(Continued)

OTHER PUBLICATIONS

International Search Report and Written Opinion for counterpart Application No. PCT/EP2019/066047, dated Aug. 22, 2019.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Mintel: "Cover Hair Root Retouch Concealer Spray," CCD Cosmética Cientifica Dermatológica, Dec. 2016.
Mintel: "Strong Hold Finishing Mist," Nexxus Beauty Products, XP55567802, Apr. 2018.

(Continued)

*Primary Examiner* — Eisa B Elhilo
(74) *Attorney, Agent, or Firm* — THE MARBURY LAW GROUP, PLLC

(57) ABSTRACT

The present invention relates to a composition for dyeing keratin fibres, comprising: a) at least one copolymer derived from the polymerization of at least one crotonic acid monomer or crotonic acid derivative and of at least one vinyl ester monomer, b) at least one fatty amine, and c) at least one pigment.

16 Claims, No Drawings

(56) References Cited

FOREIGN PATENT DOCUMENTS

| JP | 10-158541 A | 6/1998 | |
|---|---|---|---|
| WO | 02/19976 A1 | 3/2002 | |
| WO | WO 2018206453 A1 * | 11/2018 | ............ A61Q 5/065 |

OTHER PUBLICATIONS

Noll, Walter, "Chemistry and Technology of Silicones," Academic Press, New York, San Francisco, London, 1968, pp. 1-23.

Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.

Schlossman, Mitchell L., "Treated Pigments New Ways to Impart Color on the Skin," Cosmetics and Toiletries, vol. 105, Feb. 1990, pp. 53-64.

Todd, Charles, et al., "Volatile Silicone Fluids for Cosmetic Formulations," Cosmetics and Toiletries, vol. 91, Jan. 1976, pp. 29-32.

* cited by examiner

COMPOSITION FOR DYEING KERATIN FIBRES, COMPRISING AT LEAST ONE COPOLYMER DERIVED FROM THE POLYMERIZATION OF AT LEAST ONE CROTONIC ACID MONOMER AND OF AT LEAST ONE VINYL ESTER MONOMER AND A FATTY AMINE

CROSS REFERENCE TO RELATED APPLICATION

This is a national stage application of PCT/EP2019/066047, filed internationally on Jun. 18, 2019, which claims priority to French Application No. 1855867, filed on Jun. 28, 2018, both of which are incorporated by reference herein in their entireties.

The present invention relates to a composition for dyeing keratin fibres, especially the hair, comprising at least one copolymer derived from the polymerization of at least one crotonic acid monomer or crotonic acid derivative and of at least one vinyl ester monomer, at least one fatty amine and at least one pigment, and also to a dyeing process using said composition.

In the field of dyeing keratin fibres, in particular human keratin fibres, it is already known practice to dye keratin fibres via various techniques using direct dyes or pigments for non-permanent dyeing, or dye precursors for permanent dyeing.

There are essentially three types of process for dyeing the hair:
 a) "permanent" dyeing, the function of which is to afford a substantial modification to the natural colour and which uses oxidation dyes which penetrate into the hair fibre and forms the dye via an oxidative condensation process;
 b) non-permanent, semi-permanent or direct dyeing, which does not use the oxidative condensation process and withstands four or five shampoo washes; it consists in dyeing keratin fibres with dye compositions containing direct dyes. These dyes are coloured and colouring molecules that have affinity for keratin fibres,
 c) temporary dyeing, which gives rise to a modification of the natural colour of the head of hair that remains from one shampoo wash to the next, and which serves to enhance or correct a shade that has already been obtained. It may also be likened to a "makeup" process.

For this last type of dyeing, it is known practice to use coloured polymers formed by grafting one or more dyes of azo, triphenylmethane, azine, indoamine or anthraquinone nature onto a polymer chain. These coloured polymers are not entirely satisfactory, especially as regards the homogeneity of the colouring obtained and its resistance, not to mention the problems associated with their manufacture and especially with their reproducibility.

Another dyeing method consists in using pigments. Specifically, the use of pigment on the surface of keratin fibres generally makes it possible to obtain visible colourings on dark hair, since the surface pigment masks the natural colour of the fibre. The use of pigment for dyeing keratin fibres is described, for example, in patent application FR 2 741 530; when they are applied to keratin fibres, these compositions have the drawback of transferring, i.e. of becoming at least partly deposited, leaving marks, on certain supports with which they may be placed in contact and in particular clothing or the skin. This results in mediocre persistence of the applied film, making it necessary to regularly repeat the application of the composition. Moreover, the appearance of these unacceptable marks may put certain people off using this type of dyeing.

In addition, compositions for temporarily dyeing and/or making up the hair may also lead to a hair feel that is uncosmetic and/or not natural; the hair thus dyed may in particular lack softness and/or suppleness and/or strand separation.

Moreover, compositions for temporarily dyeing and/or making up the hair may also lead to the presence of residue on the head of hair when the hair is combed, which may be reflected by a dulling of the colour effect and/or lack of sheen of the head of hair. They may also lack resistance to water, in particular to rain.

There is thus still a need to obtain a composition for the temporary dyeing of keratin fibres, especially the hair, which has the advantage of forming a transfer-resistant deposit, which in particular does not become deposited, at least partly, onto supports with which the composition is placed in contact, such as the skin (in particular the hands and the face) and/or clothing, while at the same time having good cosmetic properties in terms of softness or suppleness of the hair. There is also a need to have available compositions for the temporary dyeing of keratin fibres, especially the hair, which are resistant to water, especially to rainwater, which generate little or no residue on the hair and which lead to shiny hair, while at the same time giving a uniform and chromatic colour.

Thus, the aim of the present invention is to develop a composition for dyeing keratin fibres such as the hair, which does not impair the cosmetic properties of the hair such as the softness and suppleness, while at the same time keeping the hair strands clearly individualized and having transfer-resistance properties, which is resistant to water, especially to rainwater, which generates little or no residue on the hair, leading to shiny hair, while at the same time giving a uniform and chromatic colour.

This aim is achieved with the present invention, one subject of which is a cosmetic composition comprising:
 a) at least one copolymer derived from the polymerization of at least one crotonic acid monomer or crotonic acid derivative and of at least one vinyl ester monomer,
 b) at least one fatty amine, and
 c) at least one pigment.

A subject of the invention is also a process for dyeing keratin fibres, especially human keratin fibres such as the hair, comprising the application to said fibres of a composition as defined above.

A subject of the invention is also the use of the composition as defined above, for the cosmetic treatment of, in particular for dyeing, keratin fibres, in particular human keratin fibres such as the hair.

It has been found that the composition according to the invention makes it possible to have keratin fibres, especially hair, which have a smoother feel, are softer and more supple, and which disentangle easily. This composition has good transfer resistance and the deposition onto supports with which the composition comes into contact, such as the skin and/or clothing, is limited. Furthermore, this dye composition improves the hair strand separation.

Moreover, the composition according to the invention is more resistant to water, in particular to rainwater, generates little or no residue on keratin fibres, and leads to shiny hair, giving a uniform and chromatic colouring.

The term "hair with strand separation" means hair which, after application of the composition and drying, is not stuck together (or of which all the strands are separated from each other) and thus does not form clumps of hair.

The invention is not limited to the examples illustrated. The features of the various examples may in particular be combined within variants which are not illustrated.

The expression "comprising a" should be understood as meaning "comprising at least one", unless specified to the contrary.

The expression "at least one" means "one or more".

The composition according to the invention is preferably a cosmetic composition for dyeing keratin fibres, in particular human keratin fibres such as the hair.

Crotonic Acid Copolymers

The composition according to the invention comprises at least one copolymer derived from the polymerization of at least one crotonic acid monomer or crotonic acid derivative and of at least one vinyl ester monomer, preferably at least two different vinyl ester monomers.

Preferably, the copolymer according to the invention is chosen from copolymers derived from the polymerization of at least one crotonic acid monomer and of at least one vinyl ester monomer, preferably at least two different vinyl ester monomers.

The term "crotonic acid derivative" preferably means a crotonic acid ester or a crotonic acid amide.

The term "crotonic acid derivative" preferably means a crotonic acid ester or amide, in particular:
(i) the crotonic acid esters of formula $CH_3CH=CHCOOR'_1$ with $R'_1$ representing a linear, branched or cyclic, saturated or unsaturated, optionally aromatic (aryl, aralkyl or alkylaryl) carbon-based and especially hydrocarbon-based (alkyl) chain, containing 1 to 30 carbon atoms, optionally comprising one or more functions chosen from —OH, —OR' with R' being $C_1$-$C_6$ alkyl (alkoxy), —CN, —X (halogen, especially Cl, F, Br or I); mention may be made, for example, of methyl crotonoate and ethyl crotonoate,
(ii) the crotonic acid amides of formula $CH_3CH=CHCONR'_2R''_2$ with $R'_2$ and $R''_2$, which may be identical or different, representing hydrogen or a linear, branched or cyclic, saturated or unsaturated, optionally aromatic, carbon-based and especially hydrocarbon-based (alkyl) chain, containing 1 to 30 carbon atoms, optionally comprising one or more functions chosen from —OH, —OR' with R' being $C_1$-$C_6$ alkyl (alkoxy), —CN, —X (halogen, especially Cl, F, Br or I).

The term "crotonic acid derivative" preferably means a crotonic acid ester or amide, in particular:
(i) the crotonic acid esters of formula $CH_3CH=CHCOOR'_1$ with $R'_1$ representing a linear, branched or cyclic, saturated or unsaturated, carbon-based and especially hydrocarbon-based chain, such as an alkyl, containing 1 to 30 carbon atoms, optionally aromatic, such as an aryl, aralkyl or alkylaryl, optionally comprising one or more functions chosen from —OH, —OR' with R' being $C_1$-$C_6$ alkyl, such as an alkoxy, —CN, —X, such as a halogen, especially Cl, F, Br or I; mention may be made, for example, of methyl crotonoate and ethyl crotonoate,
(ii) the crotonic acid amides of formula $CH_3CH=CHCONR'_2R''_2$ with $R'_2$ and $R''_2$, which may be identical or different, representing hydrogen or a linear, branched or cyclic, saturated or unsaturated, optionally aromatic, carbon-based and especially hydrocarbon-based chain such as an alkyl, containing 1 to 30 carbon atoms, optionally comprising one or more functions chosen from —OH, —OR' with R' being $C_1$-$C_6$ alkyl such as an alkoxy, —CN, —X such as a halogen, especially Cl, F, Br or I.

The vinyl ester monomer(s) may be chosen from the compounds of formula $CH_2=CH$—OCO—$R'_3$ with $R'_3$ representing a linear, branched or cyclic, saturated or unsaturated, optionally aromatic, carbon-based and especially hydrocarbon-based chain, containing 1 to 30 carbon atoms, optionally comprising one or more functions chosen from —OH, —OR' with R' being $C_1$-$C_6$ alkyl (alkoxy), —CN, —X (halogen, especially Cl, F, Br or I);

Mention may be made especially of vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate and vinyl trifluoroacetate.

Preferably, the copolymer according to the invention is chosen from copolymers derived from the polymerization of at least one crotonic acid monomer and of at least two different vinyl ester monomers, said vinyl ester monomers preferably being chosen from vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate and vinyl trifluoroacetate, preferably from vinyl acetate, vinyl propionate and vinyl neodecanoate, better still from vinyl acetate and vinyl neodecanoate.

More particularly, the copolymer according to the invention is chosen from copolymers derived from the polymerization of crotonic acid, vinyl acetate and vinyl propionate, copolymers derived from the polymerization of crotonic acid, vinyl acetate and vinyl neodecanoate, and mixtures thereof.

According to a particular embodiment, the copolymer of the composition according to the invention is a crotonic acid/vinyl acetate/vinyl neodecanoate terpolymer.

The copolymers according to the invention may optionally comprise other monomers such as allylic or methallylic esters, or vinyl ethers. These polymers may optionally be grafted or crosslinked.

Such polymers are described, inter alia, in French patents FR1 222 944, FR1 580 545, FR2 265 782, FR2 265 781, FR1 564 110 and FR2 439 798. Commercial products which fall into this category are the products Resyn® 28-2930 and 28-1310 sold by the company AkzoNobel (INCI names: VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name: VA/crotonates copolymer) and Mexomere® PW or PAM sold by the company Chimex (INCI name: VA/vinyl butyl benzoate/crotonates copolymer).

The total amount of copolymer(s) of crotonic acid or crotonic acid derivative according to the invention may range from 0.05% to 15% by weight relative to the weight of the composition, preferably from 0.1% to 10% by weight relative to the weight of the composition, preferably from 1% to 5% by weight relative to the weight of the composition.

Fatty Amine

The composition according to the invention comprises at least one fatty amine. The term "fatty amines" means primary, secondary or tertiary fatty amines, which are optionally (poly)oxyalkylenated, or salts thereof.

Preferably, the fatty amines comprise at least one $C_6$-$C_{30}$ hydrocarbon-based chain.

Preferably, the fatty amines according to the invention are not quaternized. Preferably, the fatty amines according to the invention are not (poly)oxyalkylenated.

Preferably, the composition according to the invention comprises at least one fatty amine chosen from tertiary fatty amines.

More preferentially, the composition according to the invention comprises one or more tertiary fatty amines chosen from fatty amidoamines.

The fatty amines that may be used in the context of the invention may be chosen from the fatty amines having the formula (K) below:

$$RN(R')_2 \quad (K)$$

in which R represents a monovalent hydrocarbon-based radical containing from 6 to 30 carbon atoms, preferably from 8 to 24 carbon atoms, and in particular a linear or branched, saturated or unsaturated and substituted or unsubstituted $C_6$-$C_{30}$ and preferably a $C_8$-$C_{24}$ alkyl radical, preferably a linear or branched $C_6$-$C_{30}$ and better still $C_8$-$C_{24}$ alkyl radical, or a linear or branched $C_6$-$C_{30}$ and preferably $C_8$-$C_{24}$ alkenyl radical; and R', which may be identical or different, represent a linear or branched, saturated or unsaturated and substituted or unsubstituted monovalent hydrocarbon-based radical containing less than 6 carbon atoms, preferably from 1 to 4 carbon atoms, preferably a methyl radical.

The fatty amines corresponding to formula (K) are chosen, for example, from dimethyllauramine, dimethylbehenamine, dimethylcocamine, dimethylmyristamine, dimethylpalmitamine, dimethylstearamine, dimethyltallowamine, dimethylsoyamine, and mixtures thereof.

The fatty amines that may be used in the context of the invention may also be chosen from fatty amidoamines, preferably the fatty amidoamines having the formula (L) below:

$$RCONHR''N(R')_2 \quad (L)$$

in which R represents a monovalent hydrocarbon-based radical containing from 5 to 29 carbon atoms, preferably from 7 to 23 carbon atoms, and in particular a linear or branched, saturated or unsaturated and substituted or unsubstituted $C_5$-$C_{29}$ and preferably a $C_7$-$C_{23}$ alkyl radical, preferably a linear or branched $C_5$-$C_{29}$ and better still $C_5$-$C_{23}$ alkyl radical, or a linear or branched $C_5$-$C_{29}$ and preferably $C_7$-$C_{23}$ alkenyl radical;

R'', which may be identical or different, represent a divalent hydrocarbon-based radical containing less than 6 carbon atoms, preferably 2 or 3 carbon atoms; and R', which may be identical or different, represent a linear or branched, saturated or unsaturated and substituted or unsubstituted monovalent hydrocarbon-based radical containing less than 6 carbon atoms, preferably from 1 to 4 carbon atoms, preferably a methyl radical.

The fatty amines corresponding to formula (L) are chosen, for example, from oleamidopropyl dimethylamine, stearamidopropyl dimethylamine sold by the company Inolex Chemical Company under the name Lexamine S13, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, avocadoamidopropyl dimethylamine, cocamidopropyl dimethylamine, minkamidopropyl dimethylamine, oatamidopropyl dimethylamine, sesamidopropyl dimethylamine, tallamidopropyl dimethylamine, olivamidopropyl dimethylamine, palmitamidopropyl dimethylamine, stearamidoethyldiethylamine, brassicamidopropyl dimethylamine, and mixtures thereof.

Preferably, the fatty amine is stearamidopropyl dimethylamine.

Preferably, the fatty amine(s) according to the invention are chosen from fatty amidoamines, preferentially from the fatty amidoamines of formula (L).

Preferably, the composition according to the invention comprises a stearamidopropyl dimethylamine.

The fatty amine(s) are present in a total amount which may range from 0.001% to 5%, preferably from 0.005% to 2%, better still from 0.01% to 1.5% by weight relative to the total weight of the composition.

Silicone

The composition may comprise at least one silicone. Preferably, the composition comprises at least two different silicones.

Preferably, the composition comprises at least one non-amino silicone and at least one amino silicone.

The silicones may be solid or liquid at 25° C. and atmospheric pressure (1.013×10$^5$ Pa), and volatile or non-volatile.

The silicones that may be used may be soluble or insoluble in the composition according to the invention; they may be in the form of oil, wax, resin or gum; silicone oils are preferred.

Silicones are especially described in detail in Walter Noll's *Chemistry and Technology of Silicones* (1968), Academic Press.

Preferably, the composition contains one or more silicones that are liquid at 25° C. and atmospheric pressure (1.013×10$^5$ Pa).

The volatile silicones may be chosen from those with a boiling point of between 60° C. and 260° C. (at atmospheric pressure) and more particularly from:

i) cyclic polydialkylsiloxanes including from 3 to 7 and preferably 4 to 5 silicon atoms, such as
  octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia;

cyclocopolymers of the dimethylsiloxane/methylalkylsiloxane type having the chemical structure:

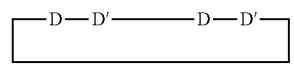

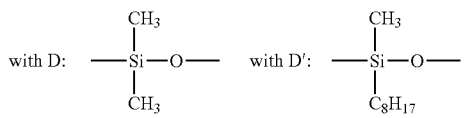

Preferably cyclomethylsiloxane.

Mention may be made of Volatile Silicone FZ 3109 sold by the company Union Carbide;

mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5 \times 10^{-6}$ m$^2$/s at 25° C., such as decamethyltetrasiloxane.

Other silicones belonging to this category are described in the article published in Cosmetics and Toiletries, Vol. 91, January 76, pages 27-32, Todd & Byers "Volatile Silicone Fluids for Cosmetics"; mention may be made of the product sold under the name SH 200 by the company Toray Silicone.

Among the non-volatile silicones, mention may be made, alone or as a mixture, of polydialkylsiloxanes and especially polydimethylsiloxanes (PDMSs), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups. Preferably, the non-volatile silicones are chosen from poly dimethyl/methylsiloxanes which are optionally oxyethylenated and oxypropylenated.

The organomodified silicones may be polydiarylsiloxanes, especially polydiphenylsiloxanes, and polyalkylarylsiloxanes, functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:

polyoxyethylene and/or polyoxypropylene groups optionally including $C_6$-$C_{24}$ alkyl groups, such as dimethicone copolyols, and especially those sold by the company Dow Corning under the name DC 1248 or the oils Silwet® L 722, L 7500, L 77 and L 711 from the company Union Carbide; or alternatively ($C_{12}$)alkylmethicone copolyols, and especially those sold by the company Dow Corning under the name Q2-5200;

substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes containing a hydroxyalkyl function;

acyloxyalkyl groups, such as the polyorganosiloxanes described in patent U.S. Pat. No. 4,957,732A;

anionic groups of the carboxylic acid type, as described, for example, in EP 186 507, or of the alkylcarboxylic type, such as the product X-22-3701E from Shin-Etsu; or alternatively of the 2-hydroxyalkylsulfonate or 2-hydroxyalkylthiosulfate type, such as the products sold by Goldschmidt under the names Abil® 5201 and Abil® 5255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning, mixtures formed from a polydimethylsiloxane with a hydroxy-terminated chain, or dimethiconol (CTFA), and from a polydimethylsiloxane, also known as dimethicone (CTFA), such as the product Xiameter ® PMX-1503 Fluid sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Preferably, the composition according to the invention comprises at least one mixture of non-amino silicones having the INCI names dimethicone and dimethiconol.

Preferably, the composition according to the invention comprises a mixture of dimethicone and dimethiconol.

The composition according to the invention preferably comprises one or more amino silicones. The term "amino silicone" denotes any silicone comprising at least one primary, secondary or tertiary amine or a quaternary ammonium group.

Preferably, the composition comprises at least one amino silicone.

The weight-average molecular masses of these amino silicones may be measured by gel permeation chromatography (GPC) at room temperature (25° C.), as polystyrene equivalent. The columns used are μ styragel columns. The eluent is THF and the flow rate is 1 ml/min. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

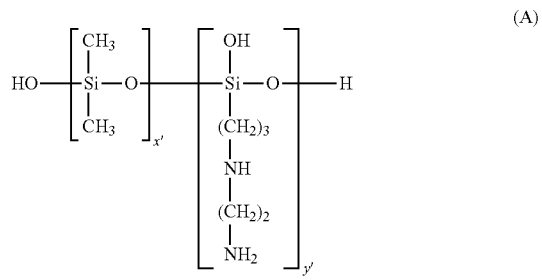

(A)

in which x' and y' are integers such that the weight-average molecular weight (Mw) is between 5000 and 500 000 approximately;

b) the amino silicones corresponding to formula (B):

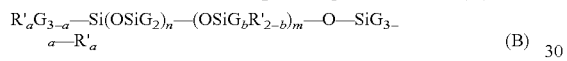

(B)

in which:

G, which may be identical or different, denotes a hydrogen atom or a phenyl, OH, $C_1$-$C_8$ alkyl, for example methyl, or $C_1$-$C_8$ alkoxy, for example methoxy, group, a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, n possibly denoting a number from 0 to 1999 and especially from 49 to 149, and m possibly denoting a number from 1 to 2000 and especially from 1 to 10;

R', which may be identical or different, denotes a monovalent radical of formula —$C_qH_{2q}L$ in which q is a number ranging from 2 to 8 and L is an optionally quaternized amine group chosen from the following groups:

—N(R")$_2$;  —N+(R")$_3$ A—;  —NR"—Q—N(R")$_2$ and —NR"—Q—N+(R")$_3$ A—, in which R", which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and A— represents a cosmetically acceptable anion, especially a halide anion such as a fluoride, chloride, bromide or iodide anion.

Preferably, the amino silicones are chosen from the amino silicones of formula (B). Preferably, the amino silicones of formula (B) are chosen from the amino silicones corresponding to formulae (C), (D), (E), (F) and/or (G) below. Preferably, the amino silicones of formula (B) are chosen from the amino silicones corresponding to formula (F).

According to a first embodiment, the amino silicones corresponding to formula (B) are chosen from the silicones known as "trimethylsilyl amodimethicone" corresponding to formula (C):

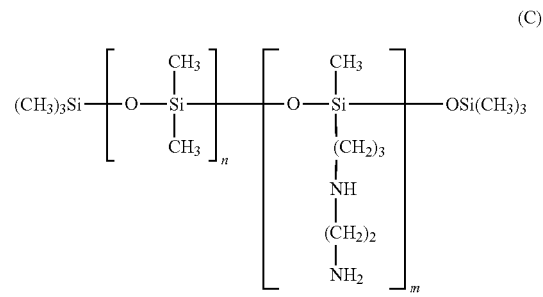

(C)

in which m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and in particular from 1 to 10.

According to a second embodiment, the amino silicones corresponding to formula (B) are chosen from the silicones of formula (D) below:

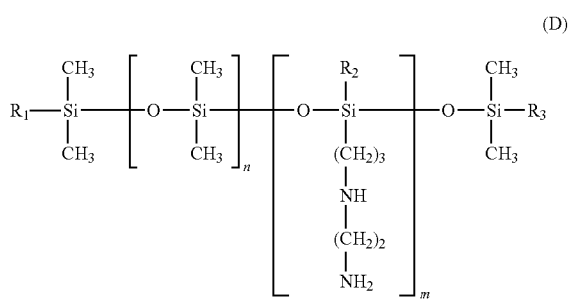

(D)

in which:

m and n are numbers such that the sum (n+m) ranges from 1 to 1000 and in particular from 50 to 250 and more particularly from 100 to 200; it being possible for n to denote a number from 0 to 999 and especially from 49 to 249 and more particularly from 125 to 175, and for m to denote a number from 1 to 1000 and especially from 1 to 10, and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular mass (Mw) of these silicones preferably ranges from 2000 to 1 000 000 and more particularly from 3500 to 200 000.

According to a third embodiment, the amino silicones corresponding to formula (B) are chosen from the silicones of formula (E) below:

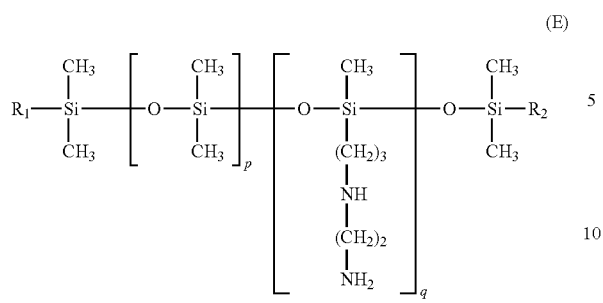

(E)

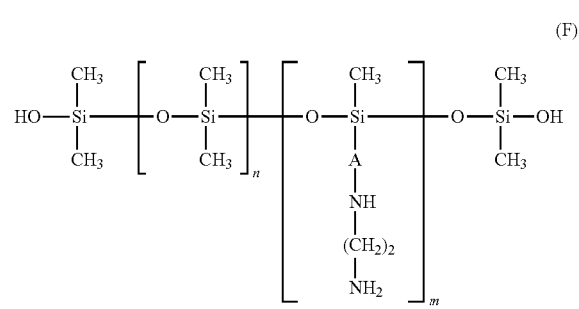

(F)

in which:

p and q are numbers such that the sum (p+q) ranges from 1 to 1000, in particular from 50 to 350 and more particularly from 150 to 250; it being possible for p to denote a number from 0 to 999 and especially from 49 to 349 and more particularly from 159 to 239, and for q to denote a number from 1 to 1000, especially from 1 to 10 and more particularly from 1 to 5;

$R_1$ and $R_2$, which may be different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones of which the structure is different from formulae (D) and (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The numerical mean size of the silicone particles in the emulsion generally ranges from 3 nm to 500 nanometres.

Preferably, in particular as amino silicones of formula (E), use is made of microemulsions with a mean particle size ranging from 5 nm to 60 nanometres (limits included) and more particularly from 10 nm to 50 nanometres (limits included). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

in which:

m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

A silicone corresponding to this formula is, for example, the Xiameter MEM 8299 Emulsion from Dow Corning (INCI name: amodimethicone and trideceth-6 and cetrimonium chloride).

According to a fifth embodiment, the amino silicones corresponding to formula (B) are chosen from the silicones of formula (G) below:

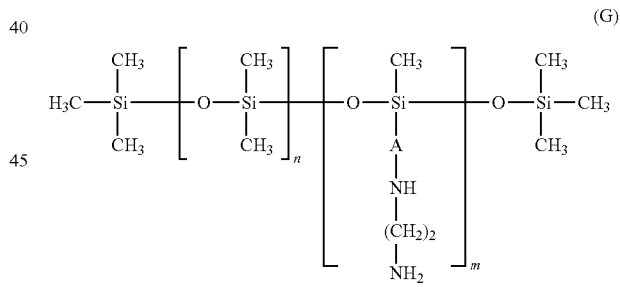

(G)

in which:

m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning.

c) the amino silicones corresponding to formula (H):

$$(R_5)_3-Si-O-\left[Si(R_5)(R_5)-O\right]_r-\left[Si(R_5)(R_6-CH_2-CHOH-CH_2-N^+(R_5)_3\ Q^-)-O\right]_s-Si-(R_5)_3 \quad (H)$$

in which:
$R_5$ represents a monovalent hydrocarbon-based radical containing from 1 to 18 carbon atoms, and in particular a $C_1$-$C_{18}$ alkyl or $C_2$-$C_{18}$ alkenyl, for example methyl, radical;
$R_6$ represents a divalent hydrocarbon-based radical, especially a $C_1$-$C_{18}$ alkylene radical or a divalent $C_1$-$C_{18}$, for example $C_1$-$C_8$, alkyleneoxy radical linked to the Si via an SiC bond;
$Q^-$ is an anion such as a halide, especially chloride, ion or an organic acid salt, especially acetate;
r represents a mean statistical value ranging from 2 to 20 and in particular from 2 to 8;
s represents a mean statistical value ranging from 20 to 200 and in particular from 20 to 50.

Such amino silicones are especially described in patent U.S. Pat. No. 4,185,087.

d) the quaternary ammonium silicones of formula (I):

$$R_8-N^+(R_7)(R_7)-CH_2-CH(OH)-CH_2-R_6-\left[Si(R_7)(R_7)-O\right]_r-Si(R_7)(R_7)-R_6-CH_2-CHOH-CH_2-N^+(R_7)(R_7)-R_8\quad 2X^- \quad (I)$$

in which:
$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;
$R_6$ represents a divalent hydrocarbon-based radical, especially a $C_1$-$C_{18}$ alkylene radical or a divalent $C_1$-$C_{18}$, for example $C_1$-$C_8$, alkyleneoxy radical linked to the Si via an SiC bond;
$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical $-R_6-NHCOR_7$;
$X^-$ is an anion such as a halide, especially chloride, ion or an organic acid salt, especially acetate;
r represents a mean statistical value ranging from 2 to 200 and in particular from 5 to 100.

These silicones are described, for example, in patent application EP-A 0 530 974.

e) the amino silicones of formula (J):

$$H_2N-(C_mH_{2m})-NH-(C_nH_{2n})-Si-\left\{O-\left[Si(R_1)(R_2)-O\right]_x-Si(R_3)(R_4)-R_5\right\}_3 \quad (J)$$

in which:
$R_1$, $R_2$, $R_3$ and $R_4$, which may be identical or different, denote a $C_1$-$C_4$ alkyl radical or a phenyl group,
$R_5$ denotes a $C_1$-$C_4$ alkyl radical or a hydroxyl group,
n is an integer ranging from 1 to 5,
m is an integer ranging from 1 to 5, and
x is chosen such that the amine number ranges from 0.01 to 1 meq/g.

f) the multiblock polyoxyalkylenated amino silicones, of the type (AB)n, A being a polysiloxane block and B being a polyoxyalkylenated block including at least one amine group.

Said silicones are preferably constituted of repeating units of the following general formulae:

$$[-(SiMe_2O)_xSiMe_2-R-N(R'')-R'-O(C_2H_4O)_a C_3H_6O)_b-R'-N(H)-R-]$$

or alternatively $$[-(SiMe_2O)_xSiMe_2-R-N(R'')-R'-O(C_2H_4O)_a (C_3H_6O)_b-]$$

in which:
a is an integer greater than or equal to 1, preferably ranging from 5 to 200 and more particularly ranging from 10 to 100;
b is an integer between 0 and 200, preferably ranging from 4 to 100 and more particularly between 5 and 30;
x is an integer ranging from 1 to 10 000 and more particularly from 10 to 5000;
R" is a hydrogen atom or a methyl;
R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a radical $CH_2CH_2CH_2OCH_2CH(OH)CH_2-$; preferentially, R denotes a radical $CH_2CH_2CH_2OCH_2CH(OH)CH_2-$;
R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2-$; preferentially, R' denotes $-CH(CH_3)-CH_2-$.

The siloxane blocks preferably represent and 50 mol % between 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may be made especially of the silicones sold under the names Silsoft A-843 or Silsoft A+ by Momentive.

g) and mixtures thereof.

Preferably, the composition according to the invention comprises at least one amino silicone having the INCI name amodimethicone, preferably as an oil-in-water emulsion with surfactants.

Preferably, the composition according to the invention comprises at least one amino silicone having the INCI name amodimethicone as an oil-in-water emulsion with surfactants, having the INCI name trideceth-6 and cetrimonium chloride.

Preferably, the composition comprises at least one non-amino silicone and/or at least one amino silicone.

Preferably, the composition comprises at least one non-amino silicone chosen from the non-amino silicones of INCI name dimethicone and dimethiconol, and/or at least one amino silicone of INCI name amodimethicone.

Preferably, the composition comprises at least one non-amino silicone chosen from the non-amino silicones of INCI name dimethicone and dimethiconol, and at least one amino silicone of INCI name amodimethicone and trideceth-6 and cetrimonium chloride.

Even more preferentially, the composition comprises at least one non-amino silicone of INCI name dimethicone, at least one non-amino silicone of INCI name dimethiconol and at least one amino silicone of INCI name amodimethicone.

The silicone(s) may be present in a total amount of at least 0.01% by weight relative to the total weight of the composition, preferably at least 0.05%, more preferentially at least 0.1%, more preferably at least 0.5%, better still at least 0.75% and even better still 1% by weight relative to the total weight of the composition.

The silicone(s) may be present in a total amount which may range from 0.01% to 10% by weight relative to the total weight of the composition, preferably from 0.05% to 5% by weight, more preferentially from 0.1% to 5% by weight relative to the total weight of the composition.

When the composition according to the invention comprises one or more amino silicones, the total amount of amino silicone(s) may range from 0.001% to 5% by weight, preferably from 0.005% to 3.5% by weight and better still from 0.01% to 2.5% by weight relative to the total weight of the composition.

When the composition according to the invention comprises one or more non-amino silicones, the total amount of non-amino silicone(s) may range from 0.001% to 5% by weight, preferably from 0.005% to 2% by weight and better still from 0.01% to 1.5% by weight relative to the total weight of the composition.

Preferably, the weight ratio of the total amount of copolymer(s) of crotonic acid or crotonic acid derivative according to the invention to the total amount of silicone(s) ranges from 0.1 to 10, more preferentially from 0.5 to 8 and better still from 1 to 5.

When the composition according to the invention comprises one or more amino silicones, the weight ratio of the total amount of copolymer(s) of crotonic acid or crotonic acid derivative according to the invention to the total amount of amino silicone(s) ranges from 0.1 to 30, more preferentially from 0.5 to 25 and better still from 1 to 20.

Thickening Polymers Containing (Meth)acrylic Acid Unit(s)

The composition according to the invention may comprise at least one thickening polymer bearing acrylic acid and/or methacrylic acid unit(s). The polymer bearing acrylic acid and/or methacrylic acid unit(s) according to the invention may be crosslinked.

Preferably, the composition according to the invention comprises one or more thickening polymers bearing acrylic acid and/or methacrylic acid unit(s).

Preferably, the polymer bearing acrylic acid and/or methacrylic acid unit(s) according to the invention is crosslinked.

According to the present invention, the term "thickening polymer" refers to a polymer which, by its presence at a concentration of 0.05% by weight, increases the viscosity of a composition into which it is introduced by at least 20 cps, preferably by at least 50 cps, at room temperature (25° C.), at atmospheric pressure and at a shear rate of 1 s$^{-1}$. The viscosity may be measured using a rheometer such as a Rheomat RM180 fitted with a no. 3 or no. 4 spindle at 25° C., at a rotational speed of 200 rpm; the measurement preferably being performed after 30 seconds of rotation of the spindle (period of time at the end of which stabilization of the viscosity and the rotational speed of the spindle is observed).

As indicated above, the composition may contain one or more thickening polymers bearing (meth)acrylic acid unit(s). The thickening polymers bearing (meth)acrylic acid unit(s) may optionally be in salified form.

In particular, the acrylic or methacrylic acid units may be in alkali metal or ammonium acrylate or methacrylate form.

The thickening polymers bearing (meth)acrylic acid unit(s) according to the invention may be anionic or amphoteric, preferably anionic.

The thickening polymers bearing (meth)acrylic acid unit(s) may be especially chosen from:
  (a) acrylic associative polymers;
  (b) preferably crosslinked acrylic acid homopolymers;
  (c) crosslinked copolymers of (meth)acrylic acid and of ($C_1$-$C_6$)alkyl acrylate;
  (d) ammonium acrylate homopolymers or copolymers of ammonium acrylate and of acrylamide.

According to the invention, the term "associative polymer" means an amphiphilic polymer including both hydrophilic units and hydrophobic units, in particular including at least one $C_8$-$C_{30}$ fatty chain and at least one hydrophilic unit.

Preferably, the composition contains an acrylic acid homopolymer, which is preferably crosslinked. Polymers of this type have the INCI name Carbomer.

a) Acrylic Associative Polymers;

Acrylic associative polymers according to the invention that may be used are associative polymers bearing (meth)acrylic acid unit(s) chosen from:
  (i) anionic amphiphilic polymers containing (meth)acrylic acid unit(s) including at least one hydrophilic unit and at least one fatty-chain unit;
  (ii) amphoteric amphiphilic polymers bearing (meth)acrylic acid unit(s) including at least one hydrophilic unit and at least one fatty-chain unit, the fatty chains containing from 10 to 30 carbon atoms.

In particular, the associative polymers bearing (meth)acrylic acid unit(s) may be chosen from:

Anionic amphiphilic polymers including at least one hydrophilic unit of (meth)acrylic acid type and at least one hydrophobic unit of ($C_{10}$-$C_{30}$)alkyl ester of unsaturated carboxylic acid type;

Amphoteric amphiphilic polymers including at least one hydrophilic unit of (meth)acrylic acid type and containing at least one fatty chain, such as copolymers of methacrylamidopropyltrimethylammonium chloride/acrylic acid/$C_{10}$-$C_{30}$ alkyl methacrylate, the alkyl radical preferably being a stearyl radical.

b) Preferably Crosslinked Acrylic Acid Homopolymers.

The polymer may be crosslinked with a crosslinking agent, in particular chosen from pentaerythritol allyl ether, sucrose allyl ether, or propylene allyl ether. Such polymers have the INCI name: Carbomer. Use may be made, for example, of the polymers sold by the company Lubrizol under the names Carbopol 980 or 981, or Carbopol Ultrez 10, or by the company 3V under the name Synthalen K or Synthalen L or Synthalen M.

c) Crosslinked Copolymers of (Meth)Acrylic Acid and of ($C_1$-$C_6$)Alkyl Acrylate;

Among the crosslinked copolymers of (meth)acrylic acid and of $C_1$-$C_6$ alkyl acrylate, mention may be made of the product sold under the name Viscoatex 538C by the company Coatex, which is a crosslinked copolymer of methacrylic acid and of ethyl acrylate as an aqueous dispersion containing 38% active material, or the product sold under the name Aculyn 33 by the company Röhm & Haas, which is a crosslinked copolymer of acrylic acid and of ethyl acrylate as an aqueous dispersion containing 28% active material. Mention may more particularly be made of the crosslinked methacrylic acid/ethyl acrylate copolymer in the form of an aqueous 30% dispersion manufactured and sold under the name Carbopol Aqua SF-1 by the company Noveon.

d) Ammonium Acrylate Homopolymers or Copolymers of Ammonium Acrylate and of Acrylamide;

Among the ammonium acrylate homopolymers that may be mentioned is the product sold under the name Microsap PAS 5193 by the company Hoechst.

Among the copolymers of ammonium acrylate and of acrylamide the product sold under the name Bozepol C Nouveau or the product PAS 5193 sold by the company Hoechst (they are described and prepared in FR-2 416 723, U.S. Pat. Nos. 2,798,053 and 2,923,692).

According to a particular embodiment of the invention, the composition comprises at least one crosslinked acrylic acid and/or methacrylic acid thickening polymer.

According to a particular embodiment of the invention, the composition comprises at least one thickening polymer bearing acrylic acid and/or methacrylic acid unit(s) chosen from crosslinked acrylic acid homopolymers.

According to the invention, the thickening polymer(s) bearing acrylic acid and/or methacrylic acid unit(s) may represent from 0.01% to 10% by weight, preferably from 0.1% to 5% by weight, preferably from 0.4% to 2% by weight relative to the total weight of the final composition.

Preferably, the weight ratio of the total amount of copolymer(s) of crotonic acid or crotonic acid derivative according to the invention to the amount of thickening polymer bearing acrylic acid and/or methacrylic acid unit(s) ranges from 0.1 to 15, more preferentially from 1 to 10 and better still from 1.5 to 8.

Pigments

The composition comprises one or more pigments.

The term "pigments" means white or coloured particles of any shape, which are insoluble in the composition in which they are present.

The pigments that may be used are especially chosen from the organic and/or mineral pigments known in the art, especially those described in Kirk-Othmer's Encyclopedia of Chemical Technology and in Ullmann's Encyclopedia of Industrial Chemistry.

They may be natural, of natural origin, or non-natural.

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" means any pigment that satisfies the definition in Ullmann's encyclopedia in the chapter on inorganic pigments. Among the mineral pigments that are useful in the present invention, mention may be made of ochres such as red ochre (clay (in particular kaolinite) and iron hydroxide (for example haematite)), brown ochre (clay (in particular kaolinite) and limonite), yellow ochre (clay (in particular kaolinite) and goethite); titanium dioxide, optionally surface-treated; zirconium oxide or cerium oxide; zinc oxide, iron oxide (black, yellow or red) or chromium oxide; manganese violet, ultramarine blue, chromium hydrate and ferric blue; metal powders such as aluminium powder or copper powder.

Mention may also be made of carbonates of alkaline-earth metals (for example of calcium or magnesium), silicon dioxide, quartz, and also any other compound used as inert filler in cosmetic compositions, provided that these compounds afford the composition colour or whiteness under the conditions in which they are used.

The pigment may be an organic pigment. The term "organic pigment" means any pigment that satisfies the definition in Ullmann's encyclopedia in the chapter on organic pigments.

The organic pigment may especially be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in the cosmetics field, provided that these compounds give the composition colour or whiteness under the conditions under which they are used, for example guanine, which, according to the refractive index of the composition, is a pigment.

In particular, the white or coloured organic pigments may be chosen from carmine, carbon black, aniline black, azo yellow, quinacridone, phthalocyanine blue, the blue pigments codified in the Colour Index under the references CI 42090, 69800, 69825, 73000, 74100, 74160, the yellow pigments codified in the Colour Index under the references CI 11680, 11710, 15985, 19140, 20040, 21100, 21108, 47000, 47005, the green pigments codified in the Colour Index under the references CI 61565, 61570, 74260, the orange pigments codified in the Colour Index under the references CI 11725, 15510, 45370, 71105, the red pigments codified in the Colour Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

Examples that may also be mentioned include pigmentary pastes of organic pigment, such as the products sold by the company Hoechst under the names:
Cosmenyl Yellow IOG: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Carmine Cosmenyl FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

The pigments in accordance with the invention may also be in the form of composite pigments, as described in patent EP 1 184 426. These composite pigments may be composed especially of particles comprising a mineral core, at least one binder, for attaching the organic pigments to the core, and at least one organic pigment which at least partially covers the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate or calcium aluminium borosilicate and aluminium.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They thus contrast with coloured pigments that afford a standard uniform opaque, semi-transparent or transparent shade.

Several types of pigment with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, coloured nacreous pigments such as mica coated with titanium and iron oxides, mica coated with iron oxide, mica coated with titanium and especially with ferric blue or with chromium oxide, mica coated with titanium and with an organic pigment as defined above, and also nacreous pigments based on bismuth oxychloride. Nacreous pigments that may be mentioned include the Cellini nacres sold by Engelhard (mica-TiO$_2$-lake), Prestige sold by Eckart (mica-TiO$_2$), Prestige Bronze sold by Eckart (mica-Fe$_2$O$_3$), and Colorona sold by Merck (mica-TiO$_2$—Fe$_2$O$_3$).

Mention may be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC108ORY by the company Toyal.

Finally, examples of nacres that may also be mentioned include polyethylene terephthalate flakes, especially those sold by the company Meadowbrook Inventions under the name Silver 1P 0.004×0.004 (silver flakes).

It is also possible to envisage multilayer pigments based on synthetic substrates, such as alumina, silica, calcium sodium borosilicate, calcium aluminium borosilicate and aluminium.

The pigments with special effects may also be chosen from reflective particles, i.e. especially from particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment by appearing to sparkle.

The reflective particles may be selected so as not to significantly alter the colouring effect generated by the colouring agents with which they are combined, and more particularly so as to optimize this effect in terms of colour rendition. They may more particularly have a yellow, pink, red, bronze, orange, brown, gold and/or coppery colour or tint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in JP-A-09188830, JP-A-10158450, JP-A-10158541, JP-A-07258460 and JP-A-05017710.

Again as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the names Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, said substrate being coated with at least one layer of at least one metal oxide, such as titanium oxide, aluminium oxide, iron oxide, cerium oxide, chromium oxide, silicon oxides and mixtures thereof Examples that may be mentioned include aluminium powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, a radiation with a wavelength of between 400 nm and 700 nm. These nanoparticles are known from the literature. In particular, they may be synthesized according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterisation of a size series of highly luminescent nanocrystallites", Journal of Physical Chemistry B, vol. 101, 1997, pages 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pages 7019-7029.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 μm, preferably between 20 nm and 80 μm and more preferably between 30 nm and 50 μm.

The pigments may be dispersed in the product by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters in particular and $C_8$ to $C_{20}$ fatty acid esters of polyols such as glycerol or diglycerol are used, such as poly(12-hydroxystearic acid) stearate with a molecular weight of approximately 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, polydimethylsiloxanes; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in the patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigment.

Preferably, the surface treatments of the pigments are chosen from the following treatments:
- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a magnesium myristate treatment, for instance the MM surface treatment sold by LCW;
- an aluminium dimyristate treatment, such as the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrogenosiloxane/perfluoroalkyl phosphate treatment, for instance the FSA surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- an acrylate copolymer treatment, for instance the APD surface treatment sold by Daito;
- a perfluoroalkyl phosphate/isopropyl titanium triisostearate treatment, for instance the PF+ITT surface treatment sold by Daito.

Preferably, the pigment is chosen from mineral or mixed mineral-organic pigments.

The amount of pigment(s) may range from 0.01% to 30% by weight, more particularly from 0.05% to 20% by weight, preferably from 0.1% to 15% by weight and preferably from 1% to 10% by weight relative to the total weight of the composition.

The composition of the invention may contain other coloured or colouring species different from the pigments according to the invention, such as direct dyes or dye precursors.

The composition according to the invention advantageously comprises water, which may preferably be present in a content ranging from 20% to 98% by weight, more preferentially from 50 to 85% by weight, relative to the weight of the composition.

Fatty Substance

The composition according to the invention may also comprise one or more non-silicone fatty substances other than the fatty amines described previously, chosen from non-silicone fatty substances that are liquid at 25° C. and at atmospheric pressure or non-silicone fatty substances that are solid at 25° C. and at atmospheric pressure.

The non-silicone fatty substances that are liquid at 25° C. and at atmospheric pressure may be chosen from $C_6$-$C_{16}$ hydrocarbons or hydrocarbons containing more than 16 carbon atoms and in particular alkanes, oils of animal origin, oils of plant origin, glycerides or fluoro oils of synthetic origin, fatty alcohols, fatty acid and/or fatty alcohol esters, non-silicone waxes, and silicones.

The fatty alcohols that may be used in the cosmetic compositions of the invention may be saturated or unsaturated, and linear or branched, and include from 6 to 30 carbon atoms and more particularly from 8 to 30 carbon atoms. Examples that may be mentioned include cetyl alcohol, cetearyl alcohol, stearyl alcohol and the mixture thereof (cetylstearyl alcohol), octyldodecanol, 2-butyloctanol, 2-hexyldecanol, 2-undecylpentadecanol, oleyl alcohol and lino leyl alcohol.

As regards the esters of fatty acids and/or of fatty alcohols, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; cetearyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

The solid non-silicone fatty substances according to the invention may be chosen from fatty alcohols, esters of a fatty acid and/or of a fatty alcohol, non-silicone waxes, ceramides, and mixtures thereof.

The term "solid fatty substance" means a fatty substance that is solid at room temperature and atmospheric pressure (25° C., 1 atm); they preferably have a viscosity of greater than 2 Pa·s, measured at 25° C. and at a shear rate of 1 s$^{-1}$.

The solid esters of a fatty acid and/or of a fatty alcohol that may be used are preferably chosen from esters derived from a $C_9$-$C_{30}$ carboxylic fatty acid and/or from a $C_9$-$C_{30}$ fatty alcohol.

Preferably, the solid esters of a fatty acid and/or of a fatty alcohol are esters of a linear or branched, saturated carboxylic acid comprising at least 10 carbon atoms, preferably from 10 to 30 carbon atoms and more particularly from 12 to 24 carbon atoms, and esters of a linear or branched, saturated monoalcohol, comprising at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from $C_9$-$C_{26}$ alkyl palmitates, in particular myristyl, cetyl or stearyl palmitate; $C_9$-$C_{26}$ alkyl myristates, such as cetyl myristate, stearyl myristate and myristyl myristate; and $C_9$-$C_{26}$ alkyl stearates, in particular myristyl stearate, cetyl stearate and stearyl stearate; and mixtures thereof, even more preferentially cetyl palmitates.

When the composition comprises one or more non-silicone fatty substances, the total content of fatty substances may range from 0.01% to 20% by weight, preferably from 0.05% to 15% by weight and better still from 0.1% to 10% by weight relative to the total weight of the composition.

Additives

The compositions may also comprise at least one agent commonly used in cosmetics, for example chosen from reducing agents, organic solvents, softeners, antifoams, moisturizers, UV-screening agents, peptizers, solubilizers, fragrances, anionic, cationic, nonionic or amphoteric surfactants, proteins and vitamins.

Surfactants

The composition may comprise one or more nonionic surfactants.

They may be chosen from alcohols, a-diols and ($C_1$-$C_{20}$) alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably containing from 2 to 30 ethylene oxide units, polyglycerolated fatty amides including on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—($C_{6-24}$ alkyl)glucamine derivatives, amine oxides such as ($C_{10-14}$ alkyl)amine oxides or N—($C_{10-14}$ acyl) aminopropylmorpho line oxides.

Mention may also be made of nonionic surfactants of alkyl(poly)glycoside type, represented especially by the following general formula:

in which:
- $R_1$ represents a linear or branched alkyl or alkenyl radical including 6 to 24 carbon atoms and especially 8 to 18 carbon atoms, or an alkylphenyl radical of which the linear or branched alkyl radical includes 6 to 24 carbon atoms and especially 8 to 18 carbon atoms,
- $R_2$ represents an alkylene radical including 2 to 4 carbon atoms,
- G represents a sugar unit including 5 to 6 carbon atoms,
- t denotes a value ranging from 0 to 10 and preferably from 0 to 4,
- v denotes a value ranging from 1 to 15 and preferably from 1 to 4.

Preferably, the alkyl(poly)glycoside surfactants are compounds of the formula described above in which:
- $R_1$ denotes a linear or branched, saturated or unsaturated alkyl radical including from 8 to 18 carbon atoms,
- $R_2$ represents an alkylene radical including 2 to 4 carbon atoms,
- t denotes a value ranging from 0 to 3 and preferably equal to 0,
- G denotes glucose, fructose or galactose, preferably glucose;
- the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$-Alkyl(poly)glucosides 1,4, and in particular decyl glucosides and caprylyl/capryl glucosides, are most particularly preferred.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, use is made of $C_8/C_{16}$-alkyl (poly)glycosides 1,4, in particular as an aqueous 53% solution, such as those sold by Cognis under the reference Plantacare® 818 UP.

The mono- or polyglycerolated surfactants preferably comprise an average number of glycerol groups ranging from 1 to 30, especially from 1 to 10, better still from 1.5 to 5. They preferably correspond to one of the following formulae:

RO[CH$_2$CH(CH$_2$OH)O]$m$H,

RO[CH$_2$CH(OH)CH$_2$O]$m$H or

RO[CH(CH$_2$OH)CH$_2$O]$m$H;

in which:
R represents a saturated or unsaturated, linear or branched hydrocarbon-based (especially alkyl or alkenyl) radical including 8 to 40 carbon atoms, especially 10 to 30 carbon atoms, optionally comprising one or more heteroatoms such as O and N; and
m is an integer ranging from 1 to 30, preferably from 1 to 10, better still from 1.5 to 6.

In particular, R may comprise one or more hydroxyl and/or ether and/or amide groups. Preferably, R is a mono- or polyhydroxylated $C_{10}$-$C_{20}$ alkyl or alkenyl radical.

Mention may be made of glyceryl stearate, sold, for example, by the company Gattefossé under the name Geleol®.

Mention may be made of polyglycerolated (3.5 mol) hydroxylauryl ether, such as the product Chimexane® NF from Chimex.

Mention may also be made of (poly)ethoxylated fatty alcohols preferably comprising one or more saturated or unsaturated, linear or branched hydrocarbon-based chains comprising 8 to 30 carbon atoms, preferably from 12 to 22 carbon atoms, optionally substituted with one or more hydroxyl (OH) groups, especially 1 to 4 hydroxyl groups.

When the chain is unsaturated, it may comprise one to three conjugated or non-conjugated carbon-carbon double bonds.

The (poly)ethoxylated fatty alcohols preferably correspond to formula (II):

$R_3$—(OCH$_2$CH$_2$)$c$OH  (II)

in which:
$R_3$ represents a linear or branched alkyl or alkenyl radical including from 8 to 40 carbon atoms and especially 8 to 30 carbon atoms, optionally substituted with one or more, especially 1 to 4, hydroxyl groups; and
c is an integer ranging from 1 to 200, especially from 2 to 150, or even from 4 to 50 and even better still from 8 to 30.

The (poly)ethoxylated fatty alcohols are more particularly fatty alcohols comprising from 8 to 22 carbon atoms, oxyethylenated with 1 to 30 mol of ethylene oxide (1 to 30 EO); mention may in particular be made of lauryl alcohol 2 EO; lauryl alcohol 3 EO; decyl alcohol 3 EO; decyl alcohol 5 EO and oleyl alcohol 20 EO.

Mention may also be made of (poly)ethoxylated plant oils such as the compounds of the INCI names PEG-40 hydrogenated castor oil and PEG-60 hydrogenated castor oil.

The nonionic surfactants may advantageously be chosen from:
(i) the monoglycerolated or polyglycerolated surfactants as presented previously,
(ii) (poly)oxyalkylenated, especially (poly)ethoxylated, fatty alcohols, and in particular those of formula (II): $R_3$—(OCH$_2$CH$_2$)$c$OH in which:
$R_3$ represents a linear or branched alkyl or alkenyl radical including from 8 to 40 carbon atoms and especially 8 to 30 carbon atoms, optionally substituted with one or more, especially 1 to 4, hydroxyl groups; and
c is an integer ranging from 1 to 200, especially from 2 to 150, or even from 4 to 50 and even better still from 8 to 30.

(iii) (poly)oxyalkylenated ($C_8$-$C_{32}$)alkyl phenyl ethers, especially comprising from 1 to 200, better still from 1 to 30 mol of ethylene oxide;
(iv) polyoxyalkylenated esters of $C_8$-$C_{32}$ fatty acids and of sorbitan, especially polyoxyethylenated esters of $C_8$-$C_{32}$ fatty acids and of sorbitan, preferably containing from 2 to 40 ethylene oxide units, better still from 2 to 20 ethylene oxide (EO) units; in particular polyoxyethylenated esters of $C_{10}$-$C_{24}$ fatty acids and of sorbitan, preferably containing from 2 to 40 ethylene oxide units, better still from 2 to 20 ethylene oxide (EO) units; and
(v) polyoxyethylenated esters of $C_8$-$C_{32}$ fatty acids, preferably containing from 2 to 150 ethylene oxide units; especially polyoxyethylenated esters of $C_{10}$-$C_{24}$ fatty acids, especially comprising 2 to 150 ethylene oxide (EO) units.
(vi) (poly)ethoxylated plant oils More preferentially, the nonionic surfactants may be chosen from:
(i) monoglycerolated or polyglycerolated surfactants
(ii) (poly)oxyalkylenated, especially (poly)ethoxylated, fatty alcohols, and
(iii) (poly)ethoxylated plant oils.

Mention may in particular be made of:
glyceryl stearate;
(poly)ethoxylated lauryl alcohol, for instance the compounds of INCI name laureth-2, laureth-3, laureth-4, laureth-10, laureth-12, laureth-23, (poly)ethoxylated cetyl alcohol, for instance the compounds of INCI name ceteth-2, ceteth-10, (poly)ethoxylated stearyl alcohol, for instance the compounds of INCI name steareth-2, steareth-10, steareth-20, (poly)ethoxylated cetearyl alcohol, for instance the compounds of INCI name ceteareth-12, ceteareth-20, ceteareth-30, ceteareth-33, (poly)ethoxylated tridecyl alcohol, for instance the compound of INCI name trideceth-6, most particularly ceteareth-20, ceteareth-12 and trideceth-6;
the compounds of INCI name PEG-40 hydrogenated castor oil, PEG-60 hydrogenated castor oil.

Preferably, the nonionic surfactants are chosen from glyceryl stearate, ceteareth-20, ceteareth-12, PEG-40 hydrogenated castor oil, and mixtures thereof.

Preferably, when they are present, the composition according to the invention comprises said nonionic surfactant(s) in an amount ranging from 0.01% to 10% by weight, especially ranging from 0.05% to 5% by weight and better still from 0.1% to 5% by weight, relative to the total weight of the composition.

Needless to say, a person skilled in the art will take care to select this or these optional additives such that the advantageous properties intrinsically associated with the formation of the coating in accordance with the invention are not, or are not substantially, adversely affected.

Presentation Form

The composition according to the invention may especially be in the form of a suspension, a dispersion, a gel, an emulsion, especially an oil-in-water (O/W) or water-in-oil (W/O) emulsion, or a multiple emulsion (W/O/W or polyol/O/W or O/W/O), in the form of a cream, a mousse, a stick, a dispersion of vesicles, especially of ionic or nonionic lipids, or a two-phase or multi-phase lotion. Preferably, the composition is in the form of a gel.

A person skilled in the art may select the appropriate presentation form, and also the method for preparing it, on the basis of his general knowledge, taking into account firstly the nature of the constituents used, especially their solubility in the support, and secondly the intended application of the composition.

Thus, the composition according to the invention generally has a viscosity at 25° C. of greater than 100 cps, preferably between 200 and 100 000 cps, more preferentially between 500 and 50 000 cps, more preferentially still between 800 and 10 000 cps, and better still between 1000 and 8000 cps, the viscosity preferably being measured at a spin speed of 200 rpm using a rheometer such as a Rheomat® RM 180 equipped with a No. 3 or 4 spindle, the measurement preferably being taken after 30 seconds of rotation of the spindle (after which time stabilization of the viscosity and of the spin speed of the spindle are observed).

Organic Solvents

The composition according to the invention may comprise one or more organic solvents.

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof Preferably, the composition according to the invention comprises one or more organic solvents.

When they are present, the organic solvents are present in proportions preferably inclusively between 0.1% and 40% by weight approximately relative to the total weight of the dye composition, more preferentially between 1% and 30% by weight approximately and even more particularly inclusively between 5% and 25% by weight relative to the total weight of the composition.

Process

A subject of the invention is also a process for dyeing keratin fibres, especially human keratin fibres such as the hair, comprising the application to said fibres of a composition as defined previously.

The dye composition according to the invention may be used on wet or dry keratin fibres, and also on any type of fair or dark, natural or dyed, permanent-waved, bleached or relaxed fibres.

According to a particular embodiment of the process of the invention, the fibres are washed before application of the composition described above.

The dyeing process is generally performed at room temperature (between 15 and 25° C.).

After the application of the composition, the fibres may be left to dry or may be dried, for example at a temperature of greater than or equal to 30° C. According to a particular embodiment, this temperature is greater than 40° C. According to a particular embodiment, this temperature is greater than 45° C. and less than 220° C.

Preferably, if the fibres are dried, they are dried, in addition to a supply of heat, with a flow of air. This flow of air during drying makes it possible to improve the individualization of the coating.

During drying, a mechanical action may be exerted on the locks, such as combing, brushing or running the fingers through. This operation may similarly be performed once the fibres have been dried, naturally or otherwise.

The drying step of the process of the invention may be performed with a hood, a hairdryer, a straightening iron, a climazone, etc.

When the drying step is performed with a hood or a hairdryer, the drying temperature is between 30 and 110° C. and preferably between 50 and 90° C.

When the drying step is performed with a straightening iron, the drying temperature is between 110 and 220° C. and preferably between 140 and 200° C.

EXAMPLES

Example 1

Compositions (g/100 g) AM: Active Material

| Composition | A (invention) |
|---|---|
| VA/crotonates/vinyl neodecanoate copolymer | 2.25 |
| Carbomer | 0.75 |
| Amodimethicone (and) trideceth-6 (and) cetrimonium chloride (Xiameter MEM-8299 Emulsion from Dow Corning) | 1.75 (1 AM) |
| Dimethicone (and) Dimethiconol (Xiameter PMX-1503 Fluid from Dow Corning) | 0.25 |
| Stearamidopropyl dimethylamine (Lexamine S-13 from Inolex Chemical Company) | 0.78 |
| CI 77491 (and) synthetic fluorphlogopite (C84-6175 Sunshine Spectral Russet from Sun) | 10 |
| Cetearyl isononanoate/ceteareth-10/ceteareth-20/ glyceryl stearate mixture (Emulgade CM from BASF) | 1.5 |
| Neutralizers | qs |
| Preserving agent, fragrance | qs |
| Ethanol | 7.5 |
| PEG-40 Hydrogenated castor oil | 1 |
| Water | qs 100 |

Protocol

Composition A is applied to locks of natural hair at a rate of 1 g of composition per gram of lock.

The locks are then combed, dried with a hairdryer and then combed again.

Results: "Cosmetic Feel" and "Transfer-Resistance" Performance

The performance qualities in terms of cosmetic feel and transfer resistance were evaluated on dried locks by five experts, in a blind test.

In 100% of the cases, the experts judged that composition A according to the invention afforded smooth locks with clearly individualized hair strands, having a pleasant cosmetic feel, especially good softness, good suppleness and absence of tackiness. Composition A according to the invention also has good transfer-resistance properties.

Example 2

Compositions (g/100 g) AM: Active Material

| Composition | A (invention) | B (comparative) |
|---|---|---|
| VA/crotonates/vinyl neodecanoate copolymer | 2.25 | 2.25 |
| Carbomer | 0.75 | 0.75 |

| Composition | A (invention) | B (comparative) |
|---|---|---|
| Amodimethicone (and) trideceth-6 (and) cetrimonium chloride (Xiameter MEM-8299 Emulsion from Dow Corning) | 1.75 (1 AM) | 1.75 (1 AM) |
| Dimethicone (and) Dimethiconol (Xiameter PMX-1503 Fluid from Dow Corning) | 0.25 | 0.25 |
| Stearamidopropyl dimethylamine (Lexamine S-13 from Inolex Chemical Company) | 0.78 | — |
| CI 77491 (and) synthetic fluorphlogopite (C84-6175 Sunshine Spectral Russet from Sun) | 10 | 10 |
| Cetearyl isononanoate/ceteareth-10/ ceteareth-20/glyceryl stearate mixture (Emulgade CM from BASF) | 1.5 | 1.5 |
| Neutralizers | qs | qs |
| Preserving agent, fragrance | qs | qs |
| Ethanol | 7.5 | 7.5 |
| PEG-40 Hydrogenated castor oil | 1 | 1 |
| Water | qs 100 | qs 100 |

Protocol

Composition A according to the invention and the comparative composition B are applied to locks of natural hair at a rate of 1 g of composition per gram of lock.

The locks are then combed, dried with a hairdryer and then combed again.

Results

Comparative composition B generates residue on the hair during combing, leading to dulling of the colour effect and a lack of sheen of the hair.

In comparison, composition A according to the invention generates little or no residue on the hair, leading to shiny hair, while at the same time giving a uniform and chromatic colour.

Example 3

Compositions (g/100 g) AM: Active Material

| Composition | C (invention) | D (comparative) |
|---|---|---|
| VA/crotonates/vinyl neodecanoate copolymer | 2.25 | 2.25 |
| Carbomer | 0.75 | 0.75 |
| Amodimethicone (and) trideceth-6 (and) cetrimonium chloride (Xiameter MEM-8299 Emulsion from Dow Corning) | 1.75 (1 AM) | 1.75 (1 AM) |
| Dimethicone (and) Dimethiconol (Xiameter PMX-1503 Fluid from Dow Corning) | 0.25 | 0.25 |
| dimethylsoyamine | 0.78 | — |
| Titanium dioxide (and) Synthetic fluorphlogopite (and) red 7 lake | 6 | 6 |
| Cetearyl isononanoate/ceteareth-10/ ceteareth-20/glyceryl stearate mixture (Emulgade CM from BASF) | 1.5 | 1.5 |
| Neutralizers | qs | qs |
| Preserving agent, fragrance | qs | qs |
| Ethanol | 7.5 | 7.5 |
| PEG-40 Hydrogenated castor oil | 1 | 1 |
| Water | qs 100 | qs 100 |

Protocol

Composition C according to the invention and the comparative composition D are applied to locks of natural hair at a rate of 1 g of composition per gram of lock.

The locks are then combed, dried with a hairdryer and then combed again.

Colorimetric measurements are made using a spectrocolorimeter Datacolor Spectraflash SF600X (D65, 10°, specular components included) in the L*a*b* system.

The chromaticity C* is calculated with the formula below:

$$C^* = \sqrt{(a^*)^2 + (b^*)^2}$$

a* indicates the axis of red/green shades and b* the axis of yellow/blue shades.

The highest the value of C* is, the more chromatic is the colour of the hair.

| | a* | b* | C* |
|---|---|---|---|
| Composition C (invention) | 40.59 | 12.84 | 42.57 |
| Composition D (comparative) | 31.89 | 10.89 | 33.70 |

Composition C according to the invention presents a value of chromaticity that is higher than the value of chromaticity of the comparative composition D.

Therefore, composition C according to the invention leads to a colour on the hair that is more chromatic than the colour obtained with the comparative composition D.

The invention claimed is:

1. A cosmetic composition comprising:
   a) at least one copolymer derived from the polymerization of at least one crotonic acid monomer or crotonic acid derivative, and of at least one vinyl ester monomer;
   b) at least one fatty amine chosen from fatty amidoamines having the formula (L) below:

RCONHR''N(R')$_2$ (L)

wherein:
   R is chosen from monovalent hydrocarbon-based radicals containing from 5 to 29 carbon atoms;
   R'', which may be identical or different, is chosen from divalent hydrocarbon-based radicals containing less than 6 carbon atoms; and
   R'', which may be identical or different, is chosen from linear or branched, saturated or unsaturated, or substituted or unsubstituted monovalent hydrocarbon-based radicals containing less than 6 carbon atoms, or mixtures thereof; and
   c) at least one pigment,
   wherein the cosmetic composition further comprises:
   at least one non-amino silicone;
   at least one amino silicone; and
   at least one non-silicone fatty substance other than fatty amines, present in a content ranging from 0.1 to 10% by weight relative to the total weight of the composition.

2. The composition according to claim 1, wherein the crotonic acid derivative is chosen from crotonic acid esters, crotonic acid amides, or mixtures thereof.

3. The composition according to claim 2, wherein:
   the crotonic acid esters are chosen from compounds of formula CH$_3$CH=CHCOOR'$_1$, wherein R'$_1$ is chosen from linear, branched, or cyclic, saturated or unsaturated, or optionally aromatic carbon-based chains, containing 1 to 30 carbon atoms, optionally comprising at least one function chosen from —OH, —OR', wherein R' is chosen from a $C_1$-$C_6$ alkyl, —CN, or —X, wherein X is a halogen; and the crotonic acid amides are chosen from compounds of formula $CH_3CH=CHCONR'_2R''_2$, wherein $R'_2$ and $R''_2$, which may be identical or different, are chosen from hydrogen, or linear, branched or cyclic, saturated or unsaturated, optionally aromatic carbon-based chains, containing 1 to 30 carbon atoms, optionally comprising at least one function chosen from —OH, —OR', wherein R' is chosen from a $C_1$-$C_6$ alkyl, —CN, or —X, wherein X is a halogen.

4. The composition according to claim 1, wherein the at least one vinyl ester monomer is chosen from vinyl acetate, vinyl propionate, vinyl butyrate or butanoate, vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate, vinyl trifluoroacetate, or mixtures thereof.

5. The composition according to claim 1, wherein the at least one copolymer is chosen from copolymers derived from the polymerization of crotonic acid, vinyl acetate, and vinyl propionate, copolymers derived from the polymerization of crotonic acid, vinyl acetate, vinyl neodecanoate, or mixtures thereof.

6. The composition according to claim 1, wherein the at least one copolymer is a crotonic acid/vinyl acetate/vinyl neodecanoate terpolymer.

7. The composition according to claim 1, wherein the at least one copolymer further comprises at least one monomer chosen from allylic or methallylic esters, vinyl ethers, or mixtures thereof.

8. The composition according to claim 1, wherein the at least one copolymer is present in an amount ranging from 0.05% to 15% by weight, relative to the weight of the composition.

9. The composition according to claim 1, wherein the at least one fatty amine is stearamidopropyl dimethylamine.

10. The composition according to claim 1, wherein the at least one fatty amine is present in a total amount ranging from 0.001% to 5%, by weight relative to the total weight of the composition.

11. The composition according to claim 1, wherein the non-amino silicones comprise dimethicone and dimethiconol; and the amino silicones comprise amodimethicone.

12. The composition according to claim 1, wherein the at least one silicon is present in a total amount ranging from 0.01% to 10% by weight, relative to the total weight of the composition.

13. The composition according to claim 1, further comprising at least one thickening polymer bearing an acrylic acid and/or a methacrylic acid unit.

14. The composition according to claim 13, wherein the at least one thickening polymer is chosen from crosslinked thickening polymers bearing an acrylic acid units.

15. The composition according to claim 13, wherein the at least one thickening polymer is present in a total amount ranging from 0.01% to 10% by weight, relative to the total weight of the composition.

16. A method for cosmetic treatment of keratin fibers, comprising applying to the keratin fibers a composition comprising:
a) at least one copolymer derived from the polymerization of at least one crotonic acid monomer or crotonic acid derivative, and of at least one vinyl ester monomer;
b) at least one fatty amine chosen from fatty amidoamines having the formula (L) below;

RCONHR'N(R')$_2$ (L)

wherein:
R is chosen from monovalent hydrocarbon-based radicals containing from 5 to 29 carbon atoms;
R", which may be identical or different, is chosen from divalent hydrocarbon-based radicals containing less than 6 carbon atoms; and
R', which may be identical or different, is chosen from linear or branched, saturated or unsaturated, or substituted or unsubstituted monovalent hydrocarbon-based radicals containing less than 6 carbon atoms, or mixtures thereof; and
c) at least one pigment,
wherein the cosmetic composition further comprises:
at least one non-amino silicone;
at least one amino silicone; and
at least one non-silicone fatty substance other than fatty amines, present in a content ranging from 0.1 to 10% by weight relative to the total weight of the composition.

* * * * *

UNITED STATES PATENT AND TRADEMARK OFFICE
CERTIFICATE OF CORRECTION

PATENT NO. : 11,980,682 B2
APPLICATION NO. : 16/975871
DATED : May 14, 2024
INVENTOR(S) : David Seneca et al.

It is certified that error appears in the above-identified patent and that said Letters Patent is hereby corrected as shown below:

In the Claims

Claim 1, Column 32, Line 46, change "R''" to -- R' --.

Claim 16, Column 34, Line 25, change "RCONHR'N(R')2(L)" to -- RCONHR"N(R')2(L) --.

Signed and Sealed this
Nineteenth Day of November, 2024

Katherine Kelly Vidal
*Director of the United States Patent and Trademark Office*